(12) United States Patent
Cong et al.

(10) Patent No.: US 9,717,428 B2
(45) Date of Patent: Aug. 1, 2017

(54) DEVICES AND METHODS FOR SENSING PHYSIOLOGICAL SIGNALS DURING STIMULATION THERAPY

(71) Applicant: Medtronic, Inc., Minneapolis, MN (US)

(72) Inventors: Peng Cong, Plymouth, MN (US); Timothy J. Denison, Minneapolis, MN (US); Forrest C. M. Pape, New Brighton, MN (US); Wesley A. Santa, Andover, MN (US); Jalpa S. Shah, Maple Grove, MN (US); Scott R. Stanslaski, Shoreview, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 381 days.

(21) Appl. No.: 14/175,491

(22) Filed: Feb. 7, 2014

(65) Prior Publication Data
US 2015/0223710 A1 Aug. 13, 2015

(51) Int. Cl.
*A61B 5/05* (2006.01)
*A61B 5/0492* (2006.01)
(Continued)

(52) U.S. Cl.
CPC ...... *A61B 5/04001* (2013.01); *A61B 5/04028* (2013.01); *A61B 5/0428* (2013.01);
(Continued)

(58) Field of Classification Search
CPC ................................................. A61B 5/04001
(Continued)

(56) References Cited

U.S. PATENT DOCUMENTS 4,149,527 A * 4/1979 Naylor ................. A61B 5/7217
600/510
2006/0259098 A1* 11/2006 Erickson .............. A61N 1/3787
607/61
(Continued)

FOREIGN PATENT DOCUMENTS

EP 1690565 8/2006
EP 1257318 12/2006
(Continued)

*Primary Examiner* — Michael C Stout
*Assistant Examiner* — Nicholas E Kolderman
(74) *Attorney, Agent, or Firm* — Withers & Keys, LLC (57) ABSTRACT

Devices and methods provide for the sensing of physiological signals during stimulation therapy by preventing stimulation waveform artifacts from being passed through to the amplification of the sensed physiological signal. Thus, the sensing amplifier is not adversely affected by the stimulation waveform and can provide for successful sensing of physiological signals. A common mode voltage is applied to the stimulation electrodes while sensing during a recharge period where the common mode voltage approximates the stimulation pulse being received at the sensing electrodes. This common mode voltage is determined based on measuring a common mode signal for at least one of the inputs of the amplifier or by deriving the proper common mode from monitoring the output signal of the amplifier to observe the elimination of artifacts during stimulation. Blanking switches may be used to blank the sensing of the peak of the recharge period should that peak be relatively large.

6 Claims, 8 Drawing Sheets

(51) Int. Cl.
  *A61B 5/04*     (2006.01)
  *A61B 5/00*     (2006.01)
  *A61B 5/0402*    (2006.01)
  *A61B 5/0428*    (2006.01)
  *A61N 1/36*     (2006.01)

(52) U.S. Cl.
  CPC ........ *A61B 5/7217* (2013.01); *A61N 1/36125* (2013.01); *A61N 1/36128* (2013.01)

(58) Field of Classification Search
  USPC .......................................................... 600/554
  See application file for complete search history.

(56) References Cited

U.S. PATENT DOCUMENTS

2008/0154350 A1*   6/2008   Julian ................... A61N 1/3956
                                607/119
2011/0025348 A1*   2/2011   Chetham ................ A61B 5/053
                                324/649
2011/0125078 A1    5/2011   Denison et al.

FOREIGN PATENT DOCUMENTS

| WO | 2006055849 | 5/2006 |
| WO | 2008020847 | 2/2008 |
| WO | 2011106660 | 9/2011 |

\* cited by examiner

DEVICES AND METHODS FOR SENSING PHYSIOLOGICAL SIGNALS DURING STIMULATION THERAPY

TECHNICAL FIELD

Embodiments provide devices and methods for sensing physiological signals. More particularly, embodiments provide devices and methods for sensing physiological signals while stimulation therapy is being conducted in proximity to the location where the physiological signals are being sensed.

BACKGROUND

Electrical stimulation therapy may be used for various forms of treatment. For example, stimulation therapy may be provided to address neurological issues such as chronic pain, tremors, and the like. In such an example, an implantable stimulation device is typically located in one location of convenience and is connected to electrical leads that are routed to a stimulation site such as within the brain, within the spinal column, within the pelvic region, or elsewhere. The electrical leads include electrodes that interface with the tissue at the stimulation site to deliver the stimulation signals from the stimulation device.

It may be useful to also sense physiological signals nearby the stimulation site. Such signals may be useful to tailor the stimulation therapy to the particular condition being treated and/or to better understand the response of the tissue nearby the stimulation site to the stimulation signals. Sensing physiological signals may be especially useful where the stimulation therapy may be at least partially controlled based on the physiological signals.

Sensing physiological signals in proximity to the stimulation site while the stimulation signals are being applied is problematic. The sensing electrodes receive the physiological signals with amplitudes in the microvolt range while also receiving the stimulation signals that have amplitudes reaching tens of volts. Thus, the physiological signal is too small relative to the stimulation signal to be detected. Additionally, the relatively large amplitudes of the stimulation pulse and recharge pulse of the stimulation signal can produce lingering voltages within the sensing circuits that overly saturate the sensing circuits and cause the physiological signals to be obscured even during periods when the stimulation pulse and the recharge pulse are not present.

This is particularly troubling for neurological stimulation systems. In neurological stimulation, the recharge phase occupies the majority of the time between stimulation pulses. For instance, a neurological stimulation signal may have a period of 7 milliseconds while the recharge phase occupies 5 of the 7 milliseconds. Thus, it is not feasible to simply blank out the sensing of the stimulation pulse and the recharge phase because there is an inadequate amount of time remaining within the period to sense the physiological signal.

SUMMARY

Embodiments address issues such as these and others by providing devices and methods that apply a common mode voltage at the stimulation electrodes during the recharge period where the common mode voltage approximates the peak of the stimulation pulse that is being captured by the sensing electrodes. In this manner, the differential from the peak of the stimulation pulse to the common mode voltage during the recharge period is relatively small such that sensing may be provided continuously including during the stimulation pulse and thereafter. Furthermore, to account for relatively large peaks during the recharge phase that may occur when large stimulation pulse amplitudes are being used, blanking of the sensed signal during the peak may also be performed.

Embodiments provide a method of sensing concurrently with stimulation with an implantable medical system having a plurality of electrodes including a pair of stimulation electrodes. The method involves measuring a signal captured from at least one electrode of the plurality that is in proximity to at least one of the stimulation electrodes during a stimulation pulse being provided through the pair of stimulation electrodes. The method involves measuring a signal captured from at least one of two sensing electrodes during a stimulation pulse and applying a voltage potential to a node that is electrically coupled to each stimulation electrode where the potential is derived from the measured signal. The method further involves sensing with the two sensing electrodes during the stimulation pulse and the recharge period to produce a differential mode signal and amplifying the differential mode signal during the stimulation pulse and the recharge period to produce an output signal.

Embodiments provide an implantable medical device that includes a stimulation engine, an amplifier, a pair of stimulation nodes, and a pair of sensing nodes coupled to the amplifier. The implantable medical device also includes an output circuit, a first pair of switches that couples the stimulation engine to the pair of stimulation nodes, and a second pair of switches that couples the output circuit to each of the stimulation nodes. The implantable medical device further includes a controller coupled to the first pair of switches, the second pair of switches, and the output circuit. The controller is configured to set the first pair of switches to a closed position and set the second pair of switches to an open position during a stimulation pulse, set the second pair of switches to the closed position and set the first pair of switches to the open position during a recharge period, measure a signal captured from the sensing nodes during the stimulation pulse, and set the output circuit to output a voltage potential that is derived from the signal captured from the sensing nodes.

Embodiments provide an implantable medical system that includes a pair of stimulation nodes, a pair of sensing electrodes, a lead body coupled to the sensing electrodes, and a stimulation engine. The implantable medical system further includes an amplifier, an output circuit, a first pair of switches that couples the stimulation engine to the pair of stimulation nodes, and a second pair of switches that couples the output circuit to each of the stimulation nodes. Additionally, the implantable medical system includes a controller coupled to the first pair of switches, the second pair of switches, and the output circuit. The controller is configured to set the first pair of switches to a closed position and set the second pair of switches to an open position during a stimulation pulse, set the second pair of switches to the closed position and set the first pair of switches to the open position during a recharge period, measure a signal captured from the sensing electrodes during the stimulation pulse, and set the output circuit to output a voltage potential that is derived from the signal captured from the sensing electrodes.

DETAILED DESCRIPTION

Embodiments provide implantable medical systems, devices, and methods that utilize during a recharge period a feedback voltage potential that is related to a common mode present on sensing electrodes as determined during a stimulation pulse. As a result, the sensing of physiological signals may continue during the stimulation pulse and the recharge period. Blanking of the sensed signal during a peak of the recharge period may be provided by some embodiments for recharge peaks that are large due to stimulation pulses with large amplitudes.

Figure 1:
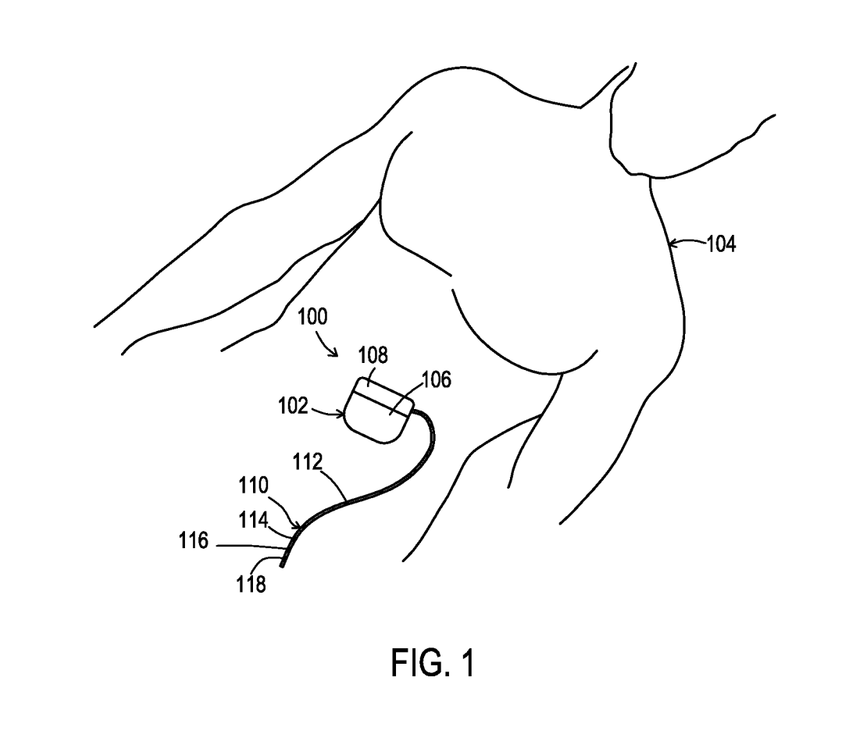
FIG. 1 shows a patient having an example of an implantable medical system for sensing physiological signals concurrently with providing stimulation signals according to various embodiments.

FIG. 1 shows an example of an operating environment for the various embodiments. An implantable medical system 100 is implanted within a body of a patient 104. The implantable medical system 100 includes a stimulation and sensing implantable medical device 102 coupled to a stimulation lead 110. The stimulation and sensing device 102 includes a conductive outer casing 106 (e.g., the device "can" or "housing") as well as a header 108 that includes a bore where a proximal end of the stimulation lead 110 is positioned. The stimulation lead 110 includes a lead body 112 and a set of electrodes 114, 116, 118 on a distal end of the lead body 112 which is positioned at a stimulation site within the body of the patient 104. While three electrodes are shown in this example, any number of electrodes may be present. The stimulation device 102 produces stimulation signals that are delivered through conductors of the stimulation lead 110 to at least one of the electrodes where those stimulation signals enter the tissue of the patient 104. Stimulation may be bipolar (between multiple ones of the electrodes of stimulation lead 110 or multiple such leads). In some embodiments, bipolar stimulation may be delivered between electrodes on different leads. Alternatively stimulation may be unipolar. The outer casing 106 may serve as an electrode where unipolar stimulation is being provided such that stimulation is delivered between an electrode on a lead and the casing 106. Stimulation could also be multipolar such that it is delivered between multiple electrodes on one or more stimulation leads as well as between at least one of the multiple electrodes and casing 106.

The stimulation and sensing device 102 senses the physiological signals during a stimulation pulse and during a subsequent recharge period. The device 102 utilizes a feedback voltage potential related to a common mode signal determined from the sensing electrodes during the stimulation phase to reduce the difference seen by a sensing amplifier from the stimulation pulse to the recharge period and thereby reduce artifacts in the sensed signal during the recharge phase. In the case of large stimulation pulses which result in large peaks in the recharge phase, the sensing function may also blank the peak of the recharge period signal. These various techniques are discussed in more detail below.

The foregoing example provides stimulation lead 110 that provides both the stimulation signal and sensing function for the physiological signal. In still another example, the one lead may be used to provide the stimulation while another lead may be used to provide both the sensing function. In yet another example, stimulation may be provided between electrodes residing on multiple different leads (e.g., between electrode 2 on lead 1 and electrode 2 on lead 2), and sensing may be performed between multiple electrodes residing on multiple different leads. The set of multiple leads providing the stimulation electrodes may, but need not, be the same set of multiple leads providing the sensing electrodes. In either case, the stimulation electrode is physically positioned between two sensing electrodes that are connected to the inputs of a differential amplifier. The stimulation electrode is approximately equidistant to the sensing electrodes so that a common mode signal on the sensing electrodes is produced during stimulation in addition to the differential signal that is ultimately amplified to produce an output representing the physiological signal being sensed.

The one or more leads used for providing the stimulation signals and for sensing the physiological signals may be of various types. In one example, a lead having a simple electrode array geometry may be used for stimulation and/or for sensing. An example of a simple electrode array geometry may include one or more ring electrodes distributed at different axial positions along the length of a lead. Another example of a simple electrode array geometry is a planar array of electrodes on a paddle lead.

In another embodiment, one or more leads used for providing the stimulation signal and for sensing the physiological signals may have a complex electrode array geometry. A complex electrode array geometry generally refers to an arrangement of stimulation electrodes at multiple non-planar or non-coaxial positions, in contrast to simple electrode array geometries in which the electrodes share a common plane or a common axis. An example of a complex electrode array geometry, in accordance with this disclosure, is an array of electrodes positioned at different axial positions along the length of a lead, as well as at different angular positions about the periphery, e.g., circumference, of the lead. In some embodiments, the electrodes in the complex array geometry may appear similar to non-contiguous, arc-like segments of a conventional ring electrode. A lead with a complex electrode array geometry may include multiple "rings" of such electrode segments. Each ring is disposed at a different axial position. Each electrode segment within a given ring is disposed at a different angular position. The lead may be cylindrical or have a circular cross-section of varying diameter. Such a lead may be referred to as a "segmented" lead.

Another example of a complex electrode array geometry is an array of electrodes positioned on multiple planes or faces of a lead. As an illustration, arrays of electrodes may be positioned on opposite planes of a paddle lead or multiple faces of a lead having a polygonal cross-section. Examples of complex array geometries are shown and described in U.S. Pat. No. 7,822,483 entitled "Electrical and Activation Field Models for Configuring Stimulation Therapy" which is assigned to the assignee of the present application and which is incorporated herein by reference. Other types of sensing and/or stimulation electrodes may be used according to the current disclosure, including conformable electrodes, cuff electrodes, segmented electrodes, or any other type of electrodes capable of forming unipolar, bipolar, or multipolar stimulation with approximately equidistant sensing electrode configurations.

The stimulation signals may be delivered using various unipolar arrangements. A unipolar stimulation arrangement generally refers to the use of an anode on the conductive outer casing 106 that sources current and one or more cathodes on one or more leads (e.g., 110) that sink current. However, embodiments may utilize an anode that is instead in a proximal position on the lead 110 which approximates the use of the outer casing 106 as the anode.

Figure 2:
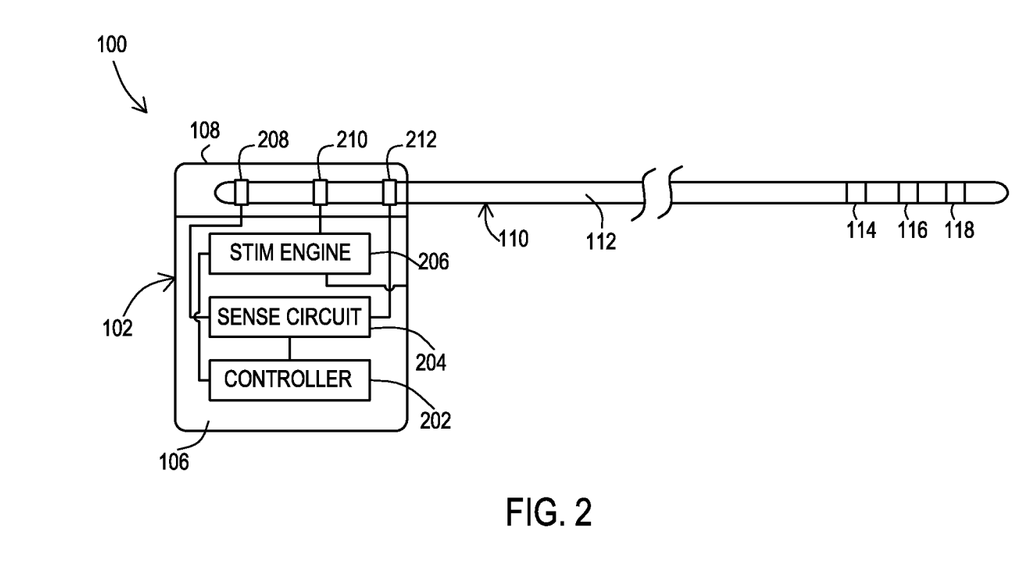
FIG. 2 shows an implantable medical system including a medical device attached to an implantable medical lead.

FIG. 2 shows the implantable medical system 100 in more detail. Here, the stimulation device 102 includes a stimulation engine 206, a sensing circuit 204, and a controller 202. A conventional stimulation engine 206 produces the stimulation pulses and recharge pulses applied to the stimulation pathway via electrical connections 210 to the lead 110 within the header block 108. The sensing circuit 204 captures the physiological signals via connections 208, 212 to the lead 110 within the header block 108.

The sensing circuit 204 captures the physiological signals in proximity to the stimulation site by determining the common mode being sensed during stimulation and applies a feedback related to the common mode during the recharge phase. The feedback may be produced as either a direct measurement of the common mode or as a value derived by sweeping a common mode to find the feedback signal that produces the best result at the amplifier output, i.e., the least artifacts from the stimulation pulse. The stimulation signal does not negatively impact the sensing circuit 204 such that the sensing circuit 204 can capture accurate physiological data during both the stimulation pulse and the recharge period.

In this example, the controller 202 orchestrates the operation of the sensing circuit 204 and the stimulation engine 206. The controller 202 activates and deactivates various phases of operation of the stimulation that occur during stimulation therapy. The phases may include a stimulation output phase where the stimulation pulse is delivered and the feedback value related to the common mode is determined, and a recharge phase that clears voltage on coupling capacitors in the stimulation path within the stimulation engine 206. Likewise, the controller 202 activates various switches of both the stimulation and the sensing circuit to allow for the common mode value to be determined during stimulation and then applied during recharge. The controller 202 may also activate other switches to blank the sensed signal during a peak of the passive recharge signal.

The controller 202 may be of various forms. For instance, the controller 202 may comprise a general purpose programmable processor that implements programming instructions to bring about the operation of the stimulation engine 206 and the sensing circuit 204. As other examples, the controller 202 may comprise a dedicated purpose processor and/or hardwired digital logic.

Figure 3:
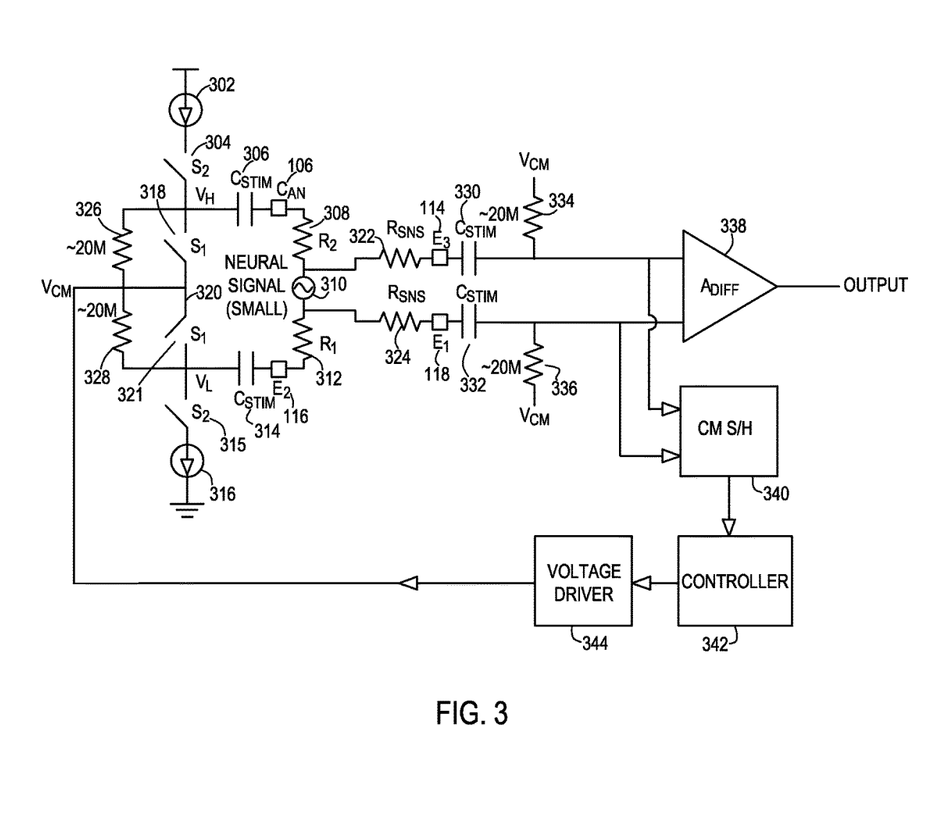
FIG. 3 shows a first example of circuitry providing the stimulation and sensing function while utilizing common mode related feedback during the recharge period.

FIG. 3 shows an example of a circuit that includes the sensing and stimulation functions and controller as illustrated in FIG. 2 that may be used to provide the stimulation pulse and the recharge period while implementing the common mode related feedback. In this particular example, the common mode feedback is based on a direct measure of the common mode signal. To provide the stimulation pulse, the implantable medical device 102 includes a first current source 302 and a second current source 316. A pair of switches 304, 315 is present and each switch is set to a closed state by a controller 342 which serves as an example of the controller 202 of FIG. 2. While maintaining the switches 304, 315 in the closed state, the controller 342 maintains the switches 318 and 321 in an open state. The node 320 is electrically referenced through a very low current trickle path including trickle resistors 326, 328 to the current sources 302, 316.

The stimulation path includes a stimulation capacitor 306 connected to the outer casing 106. The stimulation path passes through the tissue of the patient which is represented as a resistor 308 nearby the casing 106, a neural signal generator 310 representing the natural electrical behavior of the tissue, resistor 312 nearby the lead electrode 116, and a stimulation capacitor 314 connected between the electrode 116 and the current source 316. The stimulation capacitors 306, 314 gain a charge imbalance during the stimulation pulse and this imbalance is cleared during the recharge period discussed below.

The sensing function is provided via sensing paths including the sensing electrode 114 and the electrode 118. The electrode 114 senses a signal emanating from the tissue represented as neural signal source 310 and the resistor 322 while the electrode 118 senses a signal emanating from the tissue represented as the neural signal source 310 and the resistor 324. The sensing path from the electrode 114 includes a capacitor 330 connected to a first input of the differential amplifier 338, while the sensing path from the electrode 118 includes a capacitor 332 connected to a second input of the differential amplifier 338. It is to be noted that in the figures, capacitors 330, 332 are labeled Cstim even though these capacitors 330, 332 are in the sensing path because in this example, the lead electrodes are configurable to be sensing or stimulation leads and when the electrodes 114 and 118 are configured as stimulation electrodes, then the capacitors 330, 332 are in the stimulation path. Additionally, in this example the first and second amplifier inputs are referenced to a common mode voltage source via trickle resistors 334, 336 to minimize the voltage across the capacitors 330, 332.

The amplifier 338 amplifies the differential mode signal of the inputs to produce an amplified differential mode output signal which represents the sensed physiological signal. The amplifier 338 rejects the common mode signal of the inputs. Therefore, the common mode signal may be applied during recharge based on a measure of the common mode signal during the stimulation pulse to allow the sensing function to continue during and after the stimulation pulse without disturbing the amplifier 338 and therefore without stimulation pulse artifacts being prominent in the output signal of the amplifier 338.

In order to apply the common mode signal during the recharge period, a common mode sample and hold circuit 340 may be included and may be connected to either or both of the amplifier inputs. This circuit 340 captures the common mode signal being applied to either or both inputs of the amplifier during the stimulation pulse, which is essentially the amplitude of the stimulation pulse as it appears at the sensing electrodes 114, 118. The controller 342 controls the circuit 340 to capture the common mode signal during the stimulation pulse as the controller 342 is aware of the timing of the stimulation pulse. The controller 342 takes the common mode signal sample and then controls a voltage driver circuit 344, also referred to as an output circuit, to produce a voltage potential substantially equal to that common mode signal sample voltage amplitude that is then applied to the node 320. The voltage driver circuit 344 may have a variable gain that the controller 342 may adjust to approximate the common mode signal value.

During the recharge period immediately after the stimulation pulse, the controller 342 opens the switches 304, 315 and closes the switches 318, 321. This electrically couples the node 320 to the stimulation nodes, in this case the stimulation capacitors 306, 314, and therefore electrically couples the node to the stimulation electrodes including the casing 106 and the electrode 116. This causes the voltage potential being applied to the node 320 by the voltage driver 344 to be applied at both stimulation capacitors 306, 314 and hence at the casing 106 and the electrode 116. Furthermore, closing the switches 318, 321 effectively connects the capacitors 306, 314 together to provide the recharge period which eliminates the charge imbalance. The application of the common mode voltage to both of the amplifier inputs causes the common mode signal to be approximately the same amplitude as the stimulation pulse such that the amplifier 338 can continue to sense the physiological signal during and immediately after the stimulation pulse without an adverse effect. Meanwhile, the natural neural signal source 310 of the patient produces the physiological signal that appears as a differential mode signal on the inputs of the amplifier 338.

In FIG. 3, electrode 106 is described as being the can, or case, electrode such that stimulation is delivered in a monopolar manner between an electrode on lead 110 and outer casing 106. In other embodiments, the electrode 106 may instead be another electrode on a same lead (e.g., lead 110) as electrode 116, or may be an electrode on a lead other than lead 110 (not shown in the figures.) In yet another embodiment, one or more of the stimulation electrodes of FIG. 3 may each comprise multiple electrodes. In this case, a single stimulation electrode of FIG. 3 may comprise multiple electrodes on one or more leads or may instead comprise one or more electrodes on a lead and an electrode of outer casing 106 (e.g., to deliver multipolar stimulation).

Similarly, sense electrodes 114 and 118 may reside on a same lead or these electrodes may each reside on a different lead coupled to device 102. In a particular embodiment, the sense electrodes 114, 118 may each reside on different leads, and the stimulation electrodes 116 may likewise each reside on different leads, which may be the same set of leads, or a different set of leads, as the set on which the sense electrodes 114, 118 reside. In yet another embodiment one of the sense electrodes 114, 118 may reside on outer casing 106 of implantable medical device 102.

Although FIG. 3 illustrates that the same electrodes 114, 118 used to sense the neural signal are also used for determining the common mode voltage by common mode sample and hold circuit 340, this need not be the case. In another example, one or more different electrodes than those used for sensing and amplifying the neural signal may be used to determine the common mode voltage. For instance, in one particular embodiment, sensing of the neural signal may be performed between electrodes 114, 118 while the common mode voltage is determined using electrode 116. In this example, stimulation may be provided between yet a different electrode carried by a lead (not shown in FIG. 1) and the outer casing 106.

Figure 4:
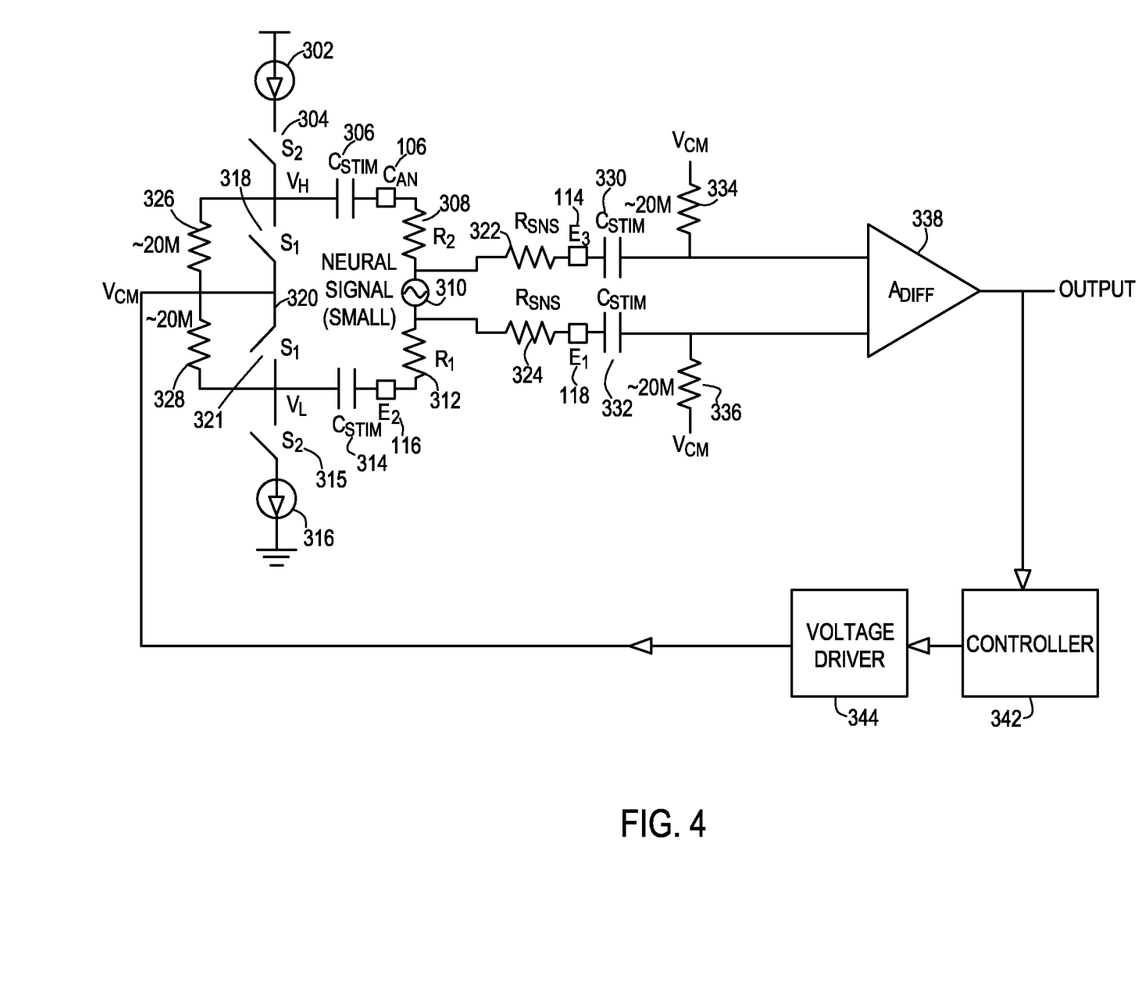
FIG. 4 shows a second example of circuitry providing the stimulation and sensing function while utilizing common mode related feedback during the recharge period.

FIG. 4 shows an alternative circuit. Rather than utilizing a sample and hold circuit at the input(s) of the amplifier 338, the controller 342 instead measures the output signal of the amplifier to look for artifacts resulting from the stimulation pulse being substantially different than the common mode voltage being applied to the amplifier inputs and node 320 during the recharge period. The controller 342 adjusts the voltage potential being applied by the voltage driver 344 to lessen the artifacts present in the output. One manner of doing so is to sweep the common voltage being applied and monitor the amplifier output for artifacts to find the voltage potential that provides the best output signal from the amplifier 338. That is, the common mode voltage can be swept to find the voltage potential that results in the smallest artifact in the output signal.

Figure 5:
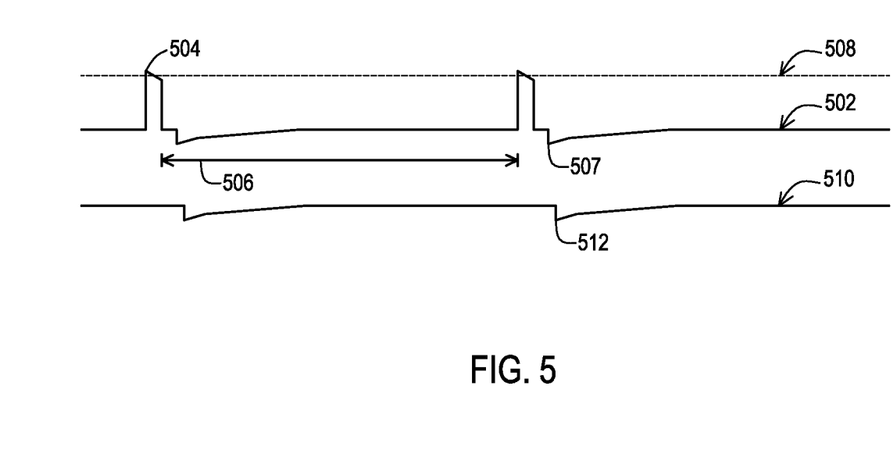
FIG. 5 shows a first example of the stimulation waveform, common mode related feedback signal, and the resulting artifact on the sensed signal.

FIG. 5 shows an example of the various signals. The stimulation pulse 504 and recharge period 506 having a peak amplitude 507 are shown as waveform 502. The common mode voltage being applied to the node 320 and hence the amplifier inputs is shown as waveform 508. The resulting amplifier output waveform 510, less the physiological signal for purposes of clarity of the artifacts present, includes primarily the artifact 512 stemming from the peak 507 of the recharge period 506. Where the peak 507 is not relatively large because the area of the stimulation pulse is not relatively large, the artifact 512 does not adversely affect the amplifier and the output signal after the artifact 512 is useful. This output signal allows for sensing of evoked compound potential (EVCP) or other stimulation induced biological signals of interest, e.g. Electromyography (EMG).

Figure 6:
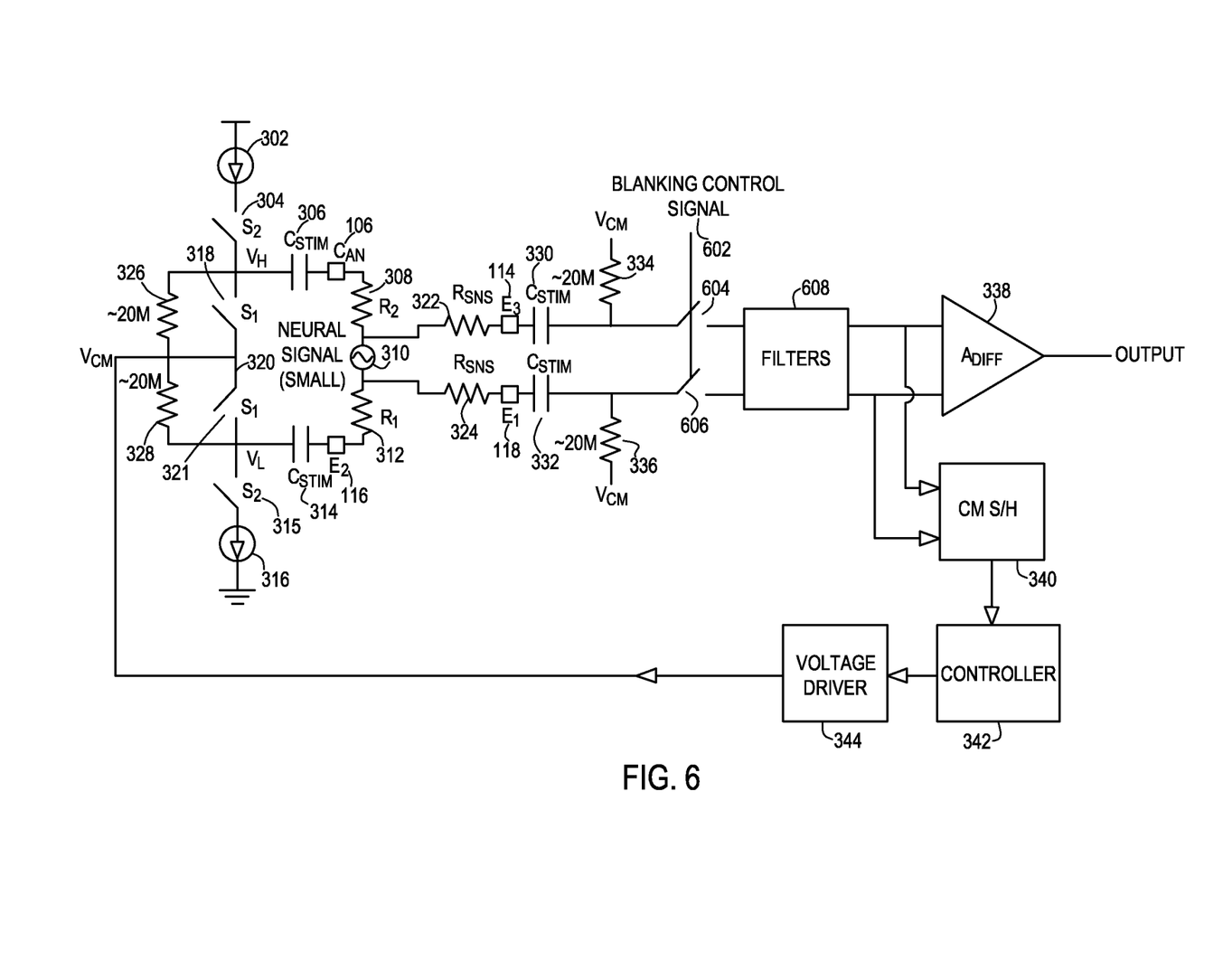
FIG. 6 shows a third example of circuitry providing the stimulation and sensing function while utilizing common mode related feedback and blanking during the recharge period.

Should the area of the stimulation pulse 504 be so large as to produce a recharge period peak 507 that does adversely affect the amplifier 338 and produce artifacts that obscure the physiological signal during a significant portion of the recharge period 506, then additional techniques may be utilized. FIG. 6 shows an example of a circuit that may address this issue. In this circuit, between the capacitors 330 and 332 and the inputs of the amplifier 338, there are blanking switches 604 and 606 that are controlled by a blanking signal 602 that may be generated by the controller 342. The blanking switches are set by the controller 342 to a closed state when sensing as well as when measuring the common mode signal on the amplifier inputs during the stimulation pulse via the sample and hold circuit 340. However, the controller 342 opens the blanking switches during the peak of the recharge period to prevent that recharge peak from creating problematic artifacts in the amplifier output.

A set 608 of high pass and low pass filters are also present between the capacitors 330 and 332 and the amplifier 338. The filters 608 include a high pass filter to decouple from DC which can occur during the blanking period. The filters 608 include a low pass filter to avoid waveform spread and to avoid a rectification effect from high frequency interferences.

Figure 7:
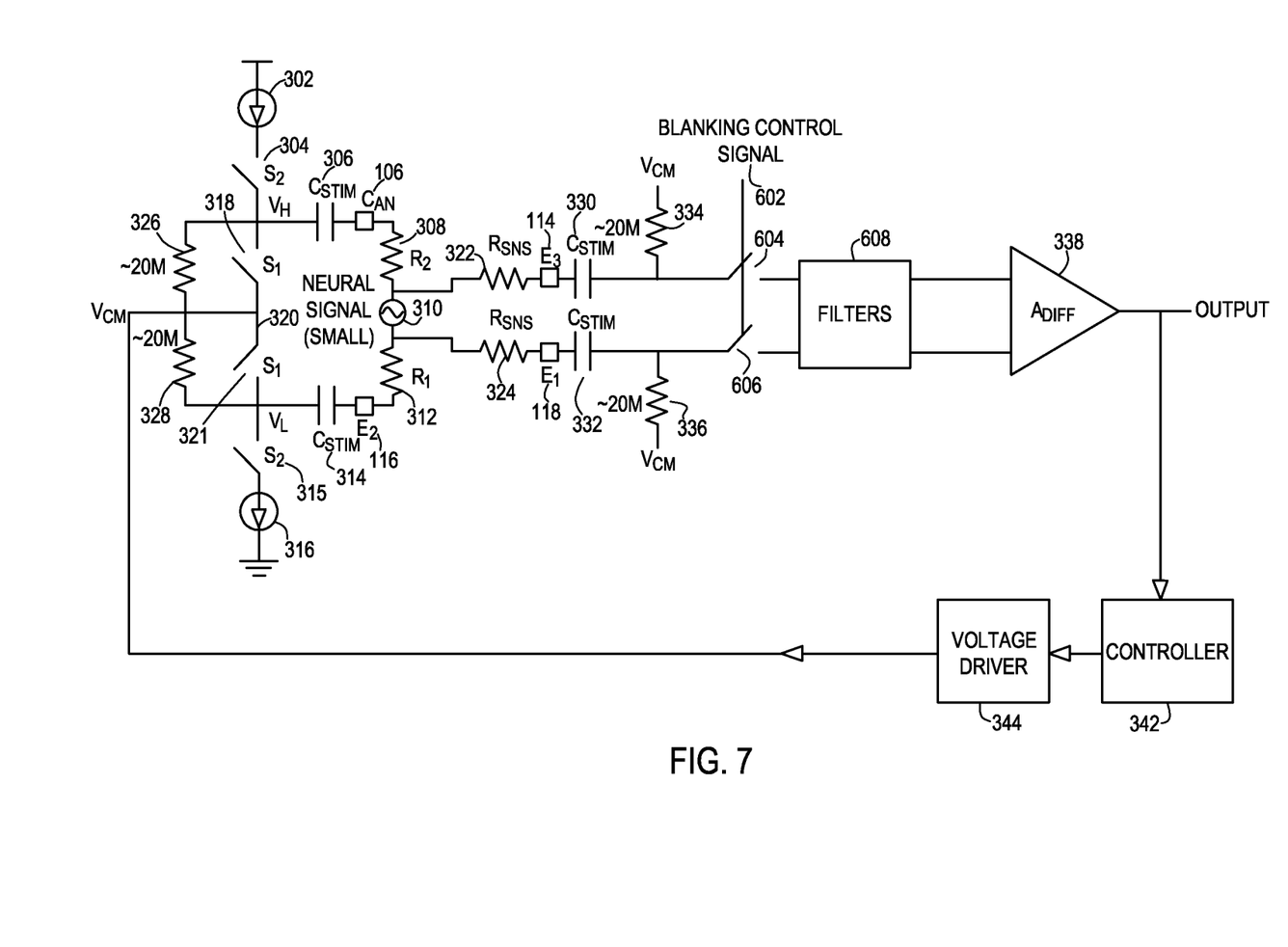
FIG. 7 shows a fourth example of circuitry providing the stimulation and sensing function while utilizing common mode related feedback and blanking during the recharge period.

In the circuit of FIG. 6, the controller 342 it utilizing the sample and hold circuit 340 that measures the common mode signal from at least one of the inputs to the amplifier 338 in the same manner described above for the circuit of FIG. 3. While the sample and hold circuit 340 is shown as being connected between the filters 608 and the amplifier input, it will be appreciated that the connection may be on the opposite side of the filters 608 as well as between the capacitors 330, 332 and the switches 602, 604. FIG. 7 shows an alternative where the blanking switches 604, 606 are being used to blank the sensed signal during the peak of the recharge period as described above for the circuit of FIG. 6. However, in FIG. 7, the controller 342 is instead monitoring the output signal from the amplifier 338 during the stimulation pulse in order to derive the common mode signal that should be output by the voltage driver 344 during the recharge period as described above for the circuit of FIG. 4.

Figure 8:
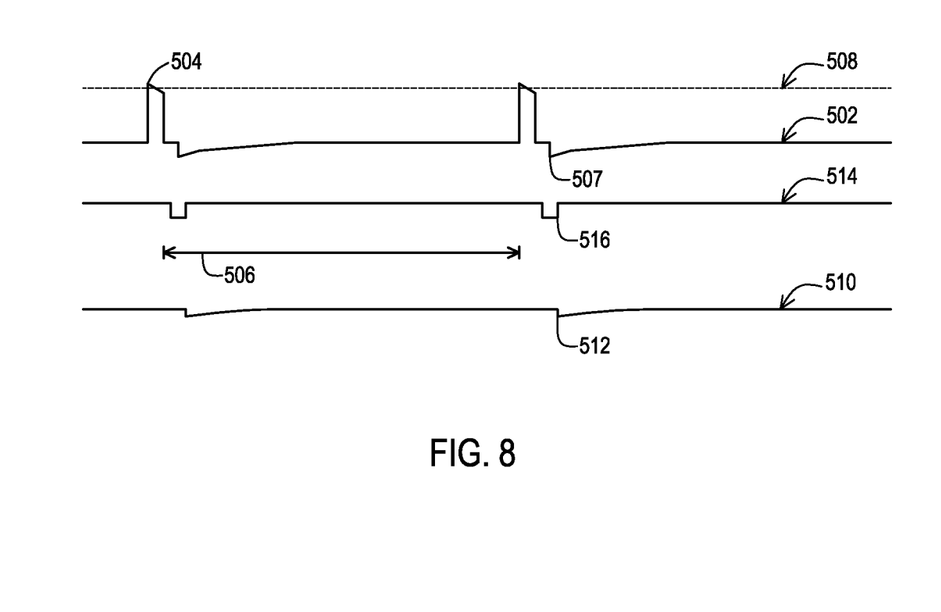
FIG. 8 shows a second example of the stimulation waveform, common mode related feedback signal, and the resulting artifact on the sensed signal.

FIG. 8 shows another example of the various signals. Similar to FIG. 5, the stimulation pulse 504 and the recharge period 506 having a peak amplitude 507 are shown as waveform 502. The common mode voltage being applied to the node 320 and hence the amplifier inputs is shown as waveform 508. A blanking control signal 514, which may be an example of the blanking control signal 602 from FIGS. 6 and 7, is shown as having a pulse 516 that occurs after the stimulation pulse has ended but prior to the start of the recharge peak 507 where that pulse 516 opens the blanking switches 604, 606 for the duration of the pulse 516. The resulting amplifier output waveform 510, less the physiological signal for purposes of clarity of the artifacts present, includes primarily the artifact 512 stemming from the remainder of the recharge period 506 occurring after the blanking signal pulse 516. Because the peak 507 has been eliminated from the output waveform 510, the artifact 512 is of a relatively small magnitude and does not adversely affect the amplifier and the output signal is useful for sensing of evoked compound potential (EVCP) or other stimulation induced biological signals of interest, e.g. Electromyography (EMG). This is the case even when the stimulation pulse 504 and peak 507 are both considered to be of a relatively large magnitude.

In the various embodiments shown in the figures discussed above, stimulation is shown to be delivered between an electrode of outer casing 106 and an electrode on a lead. However, in a manner that is similar to that described above in regards to FIG. 3, in any of the embodiments of any of the figures, stimulation may be delivered in a bipolar mode between multiple electrodes on one or more leads, or in a multipolar mode between multiple electrodes on one or more leads and an electrode on outer casing 106. Similarly, while the various figures illustrate sensing as being performed by multiple electrodes on a single lead, it will be understood that in some embodiments, sensing may be performed by electrodes on multiple leads, or between an electrode on a lead and an electrode of outer casing 106.

As previously discussed in relation to FIG. 3, although various embodiments illustrate that the same electrodes used to sense the neural signal are also used for determining the common mode voltage, this need not be the case. In any of the embodiments of any of the figures, one or more different electrodes than those used for sensing and amplifying the neural signals may be used to determine the common mode voltage. In general, the one or more electrodes used to determine the common mode voltage are electrodes different from those used to deliver the stimulation.

While embodiments have been particularly shown and described, it will be understood by those skilled in the art that various other changes in the form and details may be made therein without departing from the spirit and scope of the invention.

What is claimed is:

1. An implantable medical device, comprising:
   a stimulation engine;
   an amplifier;
   a pair of stimulation nodes;
   a pair of sensing nodes coupled to the amplifier;
   an output circuit;
   a first pair of switches that couples the stimulation engine to the pair of stimulation nodes;
   a second pair of switches that couples the output circuit to each of the stimulation nodes;
   a controller coupled to the first pair of switches, the second pair of switches, and the output circuit, the controller being configured to set the first pair of switches to a closed position and set the second pair of switches to an open position during a stimulation pulse, set the second pair of switches to the closed position and set the first pair of switches to the open position during a recharge period, measure a signal captured from the sensing nodes during the stimulation pulse, and set the output circuit to output a voltage potential that is derived from the signal captured from the sensing nodes.

2. The implantable medical device of claim 1 wherein the controller measures the signal by measuring a common mode signal being input to the amplifier and wherein the voltage potential is approximately equal to the common mode signal.

3. The implantable medical device of claim 1, wherein the controller measures the signal by measuring an output signal of the amplifier and wherein the voltage potential is derived from artifacts from the stimulation pulse in the output signal.

4. The implantable medical device of claim 1, further comprising a housing containing the controller, the amplifier, and the stimulation engine, wherein one of the stimulation nodes is the housing.

5. The implantable medical device of claim 1, wherein the controller blanks the signal being captured by the sensing nodes during a peak amplitude sensed during the recharge period by opening a third pair of switches located in series respectively between each sensing node and each corresponding input of the amplifier.

6. The implantable medical device of claim 1, further comprising a lead body coupled to the sensing nodes.

* * * * *